United States Patent [19]

Reed

[11] Patent Number: 4,704,203
[45] Date of Patent: Nov. 3, 1987

[54] CARDIOTOMY RESERVOIR APPARATUS AND METHOD

[76] Inventor: Charles C. Reed, 5934 Hornwood, Houston, Tex. 77081

[21] Appl. No.: 872,124

[22] Filed: Jun. 9, 1986

Related U.S. Application Data

[63] Continuation of Ser. No. 412,300, Aug. 27, 1982, abandoned.

[51] Int. Cl.$^4$ ............................................. B01D 19/00
[52] U.S. Cl. .................................... 210/188; 55/178; 210/335; 210/489
[58] Field of Search ............... 604/403, 404, 405, 406; 422/45, 46, 47; 210/489, 188, 335, 927; 55/178

[56] References Cited

U.S. PATENT DOCUMENTS

| | | | |
|---|---|---|---|
| 2,854,002 | 9/1958 | DeWall et al. | 422/47 |
| 3,175,555 | 3/1965 | Ling | 422/47 |
| 3,527,572 | 9/1970 | Urkiewicz | 422/47 |
| 3,768,653 | 10/1973 | Brumfield | 210/188 |
| 3,907,504 | 9/1975 | Hammond et al. | 422/46 |
| 3,935,111 | 1/1976 | Bentley | 210/927 X |
| 4,087,363 | 5/1978 | Rosemeyer et al. | 210/489 X |
| 4,116,646 | 9/1978 | Edwards | 210/436 X |
| 4,157,967 | 6/1979 | Meyst et al. | 210/489 X |
| 4,164,468 | 8/1979 | Raible | 55/178 X |
| 4,246,107 | 1/1981 | Takehaka et al. | 210/927 X |
| 4,303,530 | 12/1981 | Shah et al. | 210/489 X |

OTHER PUBLICATIONS

Bentley, BCR-3000.
Shiley Cardiotomy Reservoirs CARD and CARDF.
Travenol Cardiotomy Blood Reservoir 5M0305.

Primary Examiner—Frank Spear
Attorney, Agent, or Firm—Workman, Nydegger & Jensen

[57] ABSTRACT

A novel cardiotomy reservoir apparatus and method for use in an extracorporeal blood circuit which provides for the effective defoaming of blood that has been aspirated from a patient during surgery. The apparatus includes an outer receptacle, which is preferably generally cylindrical in shape, the receptacle having at least one inlet formed in the top thereof, an outlet formed in the bottom thereof, and a vent port. The receptacle contains a defoaming means which substantially occupies the entire interior volume of the receptacle, and which has an increasing density in the direction of blood flow through the receptacle. In addition, the cardiotomy reservoir of the present invention may be used with an external blood filter and the outlet of the reservoir receptacle has a valve formed therein to facilitate rapid and safe replacement of the external filter in the event that it becomes occluded.

33 Claims, 5 Drawing Figures

CARDIOTOMY RESERVOIR APPARATUS AND METHOD

This application is a continuation of application Ser. No. 412,300, filed Aug. 27, 1982, now abandoned.

BACKGROUND

1. Field of the Invention

The present invention relates to methods and apparatus in the field of cardiotomy perfusion, and in particular, it is directed to cardiotomy reservoirs which are used in extracorporeal blood circuits.

2. The Prior Art

There are a wide variety of medical and surgical procedures in which a patient's blood is conducted extracorporeally through a blood circuit for treatment and thereafter returned to the patient. Typical extracorporeal blood circuits include, for example, cardiopulmonary bypass and extracorporeal hemodialysis.

Effective circulation and control of a patient's blood are essential to successful heart surgery. In modern surgical procedures, blood is circulatd through the patient mechanically by establishing a cardiopulmonary bypass circuit in which the blood is forced through a bloodline or tube with a blood pump. This circuit removes blood from the patient, oxygenates the blood, and then returns the blood to the patient.

In addition, blood which accumulates in the patient's pericardium or heat cavities during the course of surgery is transported away from the surgical site. This is generally accomplished by means of a "cardiotomy sucker" which aspirates the blood from the areas of accumulation. During an operation of only thirty minutes, as much as 250,000 cubic centimeters of blood may be aspirated from the patient through the "cardiotomy sucker." Consequently, unless it can be successfully returned to the patient, this aspirated blood must be replaced by blood from other sources. In attempting to return this aspirated blood to the patient, however, one encounters of number of obstacles.

Blood removed from the surgical site through a "cardiotomy sucker" invariably contains tissue fragments, blood clots and other debris which prevent the blood from being returned directly to the patient through the cardiopulmonary bypass circuit. This difficulty can generally be minized by allowing the blood to pass through filters which remove all particles larger than a predetermined size, for example, twenty (20) microns. However, this filter will sometimes become occluded and must, consequently, be replaced.

A somewhat more difficult obstacle to recycling aspirated blood is due to the fact that blood which is removed from the surgical site through a "cardiotomy sucker" has a substantial amount of air bubbles suspended within it, thereby resulting in a foam-like solution. Oxygenators which are used in the cardiopulmonary bypass circuit have traditionally had some limited defoaming capability, because small air bubbles remain in the blood after the oxygenating process. However, aspirated blood differs greatly from oxygenator blood for which the oxygenator defoamer was designed. Although bubbles are present in both oxygenator and aspirated blood, the bubbles contained in oxygenator blood are typically within the same, specific micron range as the bubbles produced by the oxygenator. Aspirated blood, on the other hand, contains bubbles with no such size uniformity, and the quantity of bubbles may vary from a steady stream to a froth. As a result, defoaming aspirated blood is significantly more difficult than defoaming oxygenator blood and has provided a significant challenge to those skilled in the art.

In order to more effectively prepare aspirated blood for return to the patient, a device known as a cardiotomy reservoir has been used. Cardiotomy reservoirs currently in use have the capability of holding large volumes of blood separate from the main extracorporeal cardiopulmonary bypass circuit. Many of the cardiotomy reservoirs currently in use also include internal filters which separate out the above-mentioned debris. Typical prior art cardiotomy reservoirs also contain a small defoaming element which defoams the blood as it passes through the cardiotomy reservoir. After the blood has been so treated, it is then recycled to the patient through the cardiopulmonary bypass circuit.

Although the cardiotomy reservoirs presently in use have greatly improved the quality of the blood which is returned to the patient, current cardiotomy reservoirs have proven inadequate in many respects. Current cardiotomy reservoirs use a defoaming substance which is composed of the same material used in the defoamer within the oxygenator. This defoamer, which is a uniform single density defoamer, cannot effectively defoam aspirated blood where there are a wide variety of sizes and quantities of air bubbles suspended within the blood.

Additionally, the design of present cardiotomy reservoirs allows blood to pass quite rapidly through the reservoir. That blood is, therefore, not in contact with the defoaming element for any significant length of time and this results in inadequate defoaming of the blood. Even if the outflow of blood from current cardiotomy reservoirs is intentionally interrupted, significant volumes of blood are held in the lower portion of the cardiotomy reservoir and are not in contact with the defoamer element at all. Consequently, the temporary interruption of blood outflow from present cardiotomy reservoirs does significantly improve their defoaming capability.

Finally, cardiotomy reservoirs which include internal filters occasionally clog due to excessive debris and/or blood clots resulting from inadequate heparinization, accelerated metabolism of the heparin, or blood coagulopathy. When the internal filtr of the cardiotomy reservoir becomes clogged, the entire cardiotomy reservoir must be changed. This interrupts and disrupts the cardiotomy reservoir circuit. Equally important, the blood trapped within the clogged cardiotomy reservoir cannot always be recovered and returned to the extracorporeal circuit; hence, significant volumes of blood must sometimes be discarded. Even if the trapped blood is recovered, it will often not be used because there is an insufficient guarantee of sterility. In addition, there is often even no attempt to recover this trapped blood, because the time needed to recover the blood to the extracorporeal circuit may be too lengthy. Each of the above-mentioned situations adds significantly and dangerously to the normal risk involved in heart surgery.

Accordingly, it would be a significant improvement in the art to provide a cardiotomy reservoir having a defoamer which is specifically designed to handle blood containing suspended air bubbles of many sizes, such as blood aspirated during heart surgery, Additionally, it would be an improvement in the art to provide a cardiotomy reservoir in which the defoamer is always in substantial contact with the blood which is located within the reservoir. Further, it would be an improvement in the art to provide a cardiotomy reservoir which would allow for the rapid replacement of a clogged filter, without compromising asepsis or blood recoverability. Finally, it would be an improvement in the art to provide a method for defoaming aspirated blood which adequately separates the air from the blood while minimizing the risk to the patient incident to the defoaming process. Such a novel cardiotomy reservoir apparatus and method is described and claimed herein.

SUMMARY AND OBJECTS OF THE INVENTION

The present invention is directed to an improved cardiotomy reservoir which has at least one inlet and one outlet. The defoamer within the reservoir is graduated in density and substantially occupies the entire interior of the cardiotomy reservoir. The cardiotomy reservoir is to be used with an external filter and has a valve for temporarily preventing blood outflow from the reservoir. Thus, in the event that the external filter becomes occluded, it may be quickly and easily replaced while the blood is maintained in the cardiotomy reservoir.

The novel cardiotomy reservoir of the present invention provides for the effective defoaming of aspirated blood even though there is a wide variety of sizes and quantities of bubbles suspended within the blood stream. The defoamer used in the novel cardiotomy reservoir of the present invention is constantly in contact with the aspirated blood from the time the blood enters the cardiotomy reservoir until it leaves the reservoir and is transported through the cardiopulmonary bypass circuit to the patient. Finally, the cardiotomy reservoir is designed to preserve the sterility and the recoverability of blood, as well as to minimize the dnager to the patient in the event that a filter change becomes necessary during the course of the operation.

It is, therefore, a primary object of the present invention to provide a cardiotomy reservoir which is efficient and effective in defoaming blood aspirated from a patient during surgery.

It is another object of the present invention to provide a blood defoamer which is capable of separating a variety of sizes and quantities of air bubbles suspended in the blood.

It is a further object of the present invention to provide a defoamer for use in a cardiotomy reservoir which is in substantial contact with the blood during its residence in the reservoir, thereby maximizing the defoaming accomplished within the reservoir.

It is a still further object of the present invention to provide a cardiotomy reservoir which facilitates rapid replacement of the blood filter while at the same time minimizing blood loss caused by filter occlusion.

It is still another object of the present invention to provide an improved method for defoaming blood which is effective in removing air bubbles from aspirated blood and which minimizes the danger to the patient incident to the defoaming process.

These and other objects and features of the present invention will become fully apparent from the following description and appended claims taken in conjunction with the accompanying drawings.

DETAILED DESCRIPTION OF THE PREFERRED EMBODIMENTS

The presently preferred embodiments of the invention will be best understood by reference to the figures wherein like parts are designated with like numerals throughout.

Figure 1:
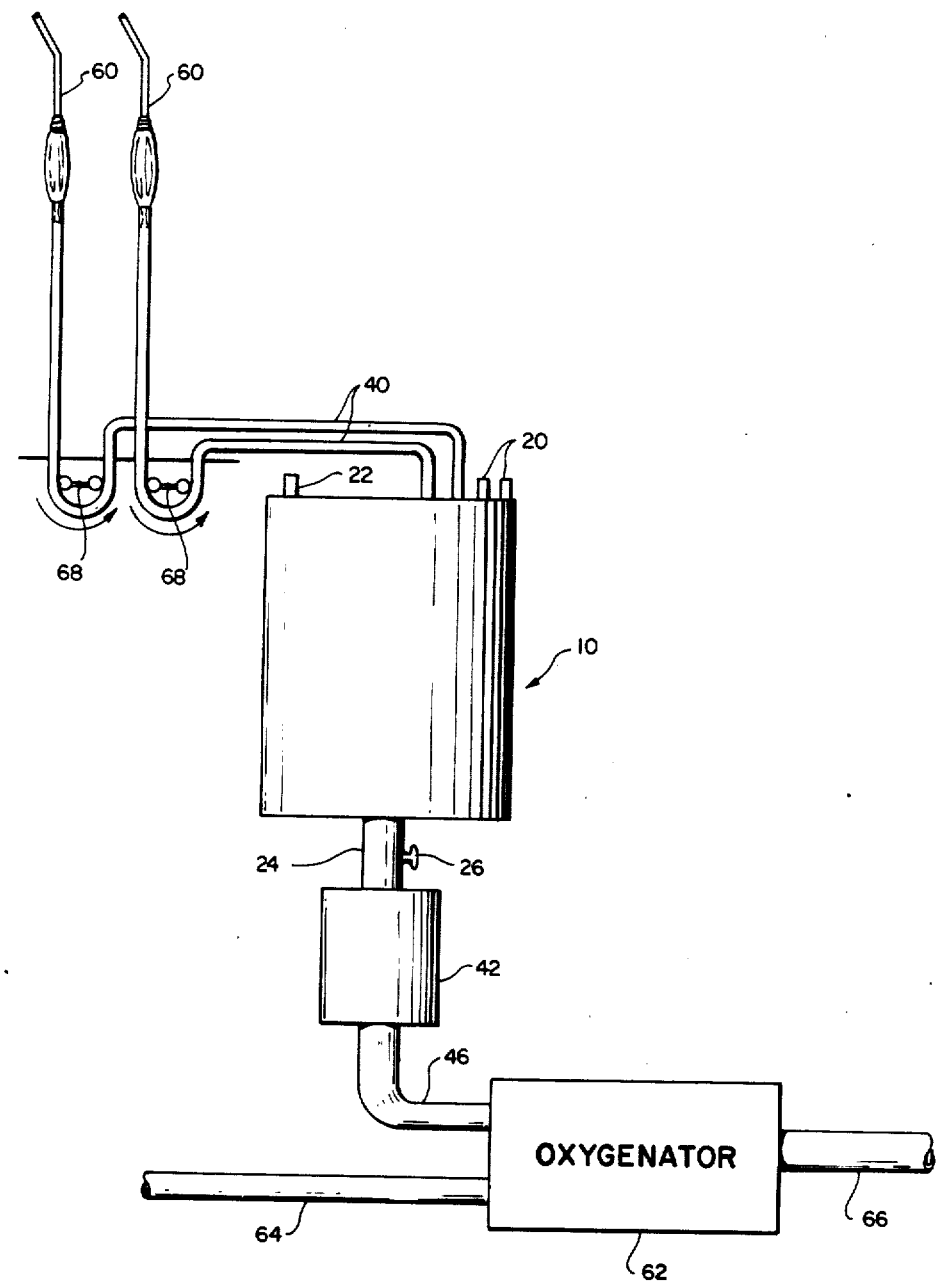
FIG. 1 is a schematic representation of an extracorporeal blood circuit incorporating a cardiotomy reservoir within the scope of the present invention.

FIG. 1 illustrates a typical extracorporeal circuit in which a cardiotomy reservoir within the scope of the present invention may be used. WIth specific reference to FIG. 1, the main cardiopulmonary bypass circuit withdraws blood from the patient through venous return line 64 which is connected to the vein of the patient through a cannula or other suitable means. This blood is then oxygenated in oxygenator 62 and returned to the patient through arterial line 66.

Cardiotomy reservoir 10 works together with the main cardiopulmonary bypass circuit to allow blood which has been scavaged from the operative field to be recycled back to the patient. Blood is scavaged from the operative field by means of one or more suckers 60 which aspirate blood and debris from the operative field by means of suction; this suction is typically provided by roller pumps 68. A separate roller pump 68 is used for each sucker 60 and each roller pump 68 pumps at a rate of about three to four liters per minute. Thus, it will be appreciated that a significant quantity of air is drawn into suckers 60 and mixed with the aspirated blood.

The scavaged blood is transported from suckers 60 through respective intake lines 40 to inlet ports 20 of cardiotomy reservoir 10. Although two intake lines are illustrated in FIG. 1, it will be appreciated that a greater or lesser number may also be used, depending on the specific surgical procedures involved, the amount of blood to be aspirated, and the surgeon's personal preference.

Inside cardiotomy reservoir 10, the blood is defoamed, with the liberated gases escaping through vent port 22. The blood then drains cardiotomy reservoir 10 under the force of gravity and exits cardiotomy reservoir 10 through outlet port 24 at a rate of between about 1,000 and about 1,500 cubic centimeters per minute. Upon exiting cardiotomy reservoir 10, the blood passes through external filter 42 and cardiotomy return line 46 into oxygenator 62. In oxygenator 62, the blood from cardiotomy reservoir 10 combines with the blood from venous return line 64 and passes through oxygenator 62 and is returned to the patient through arterial line 66.

Figure 2:
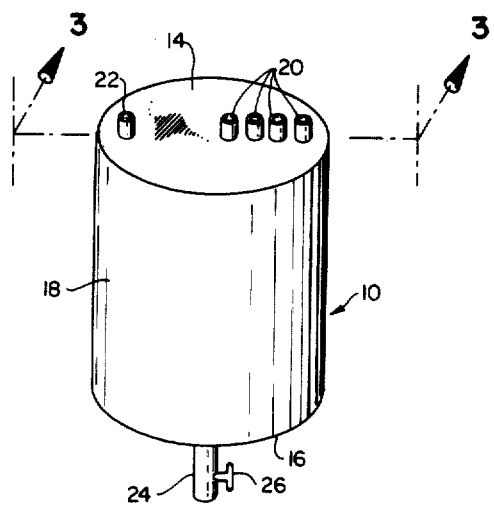
FIG. 2 is a perspective view of a preferred embodiment of the cardiotomy reservoir of the present invention.

Referring now more specifically to the particular structure of the cardiotomy reservoir of the present invention, a cardiotomy reservoir within the scope of the present invention is illustrated generally as 10 in FIG. 2. Although cardiotomy reservoir 10 as shown in FIG. 2 is generally cylindrical in shape, it will be readily appreciated that a variety of shapes may be used to achieve the objects and purposes of the novel apparatus and methods and that the cardiotomy reservoir of the present invention is, thus, not restricted to any particular shape. Generally, the specific shape of cardiotomy reservoir 10 is selected so as to facilitate the manufacturing process.

As shown in FIG. 2, cardiotomy reservoir 10 has an outer receptacle consisting of a cylindrical sidewall 18, a top 14, and a bottom 16. This outer receptacle is preferably constructed of a rigid, transparent material so that cardiotomy reservoir 10 will retain its shape during use and the contents of cardiotomy reservoir 10 are visible. While it is recognized that the outer receptacle could be made of either glass or a plastic material, it will also be appreciated that glass is generally a less desirable construction material because of the possibility that a glass cardiotomy reservoir will break and shatter in the operating room.

The outer receptacle of a presently preferred embodiment of cardiotomy reservoir 10 is constructed of a hard, plastic material, such as LEXAN, which is polycarbonate. Such a receptacle may be formed, for example, by injection molding the entire outer receptacle or by extruding cylindrical sidewall 18 and injection molding top 14 and bottom 16 on the ends thereof. It is recognized, however, that a suitable outer receptacle may also be formed of a softer, deformable material, such as, for example, polyvinylchloride, which is radio frequency welded at the seams, or silicon rubber, which is bonded at the seams.

In a preferred embodiment of cardiotomy reservoir 10 illustrated in FIG. 2, top 14 of cardiotomy reservoir 10 is equipped with several inlet ports 20 which are generally tubular in shape and provide access to the interior of cardiotomy reservoir 10. Inlet ports 20 thus provide a means for connecting cardiotomy reservoir intake lines 40, which are attached to suckers 60 (see FIG. 1), to cardiotomy reservoir 10. As mentioned above, a plurality of suckers 60 are normally used during surgery. For convenience of illustration, four inlet ports 20 are illustrated in FIG. 2; however, it will be appreciated that a greater or lesser number of inlet ports 20 may be provided without departing from the teachings of the present invention.

Top 14 is also equipped with vent port 22. Vent port 22 likewise communicates with the interior of cardiotomy reservoir 10, thereby allowing air which has been liberated from the blood during the defoaming process to escape from cardiotomy reservoir 10. A suction force is sometimes supplied by connecting vent port 22 to a suction source in the operating room. However, unless this suction is kept very low (less than about 15 centimeters H$_2$O), the hemolysis produced by the system is greater than that produced by a system which uses roller pumps. As a result, many surgeons find this suction limitation unacceptable and, consequently, rollers pumps 68 are used in most cardiopulmonary bypass circuits (see FIG. 1). Under these conditions, vent port 22 is merely vented to atmosphere conditions.

Bottom 16 of cardiotomy reservoir 10 has an outlet port 24 formed therein which also communicates with the interior of cardiotomy reservoir 10 and with cardiotomy return line 46. Additionally, outlet port 24 has a valve 26 formed therein, which may be either an automatic or a manually operated valve. By closing valve 26, outlet port 24 may be occluded thereby preventing fluid flow from the receptacle. With the blood flow thus interrupted, a clogged external filter 42 (see FIG. 1) may be quickly and easily replaced, as explained more fully below. Also, as will be more apparent from the discussion which follows, the temporary closing of valve 26 does not interrupt the defoaming process since the blood within the receptacle remains in contact with the defoaming material. Fluid flow through the receptacle may then be reestablished by returning valve 26 to the open position.

Figure 3:
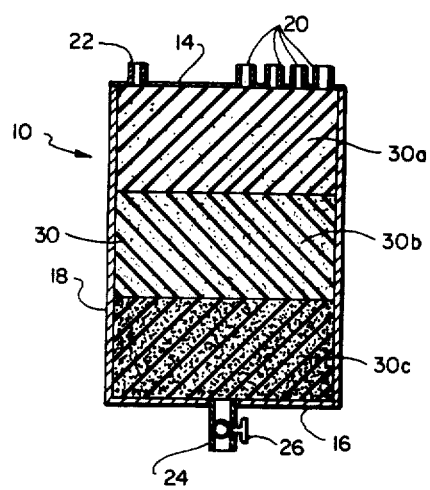
FIG. 3 is a vertical cross-sectional view of a preferred embodiment of the cardiotomy reservoir of the present invention in which the internal construction of the cardiotomy reservoir is illustrated.

As shown best in FIG. 3, the defoamer, which is illustrated generally as 30, is positioned inside the receptacle and extends from top 14 to bottom 16 of the receptacle, so as to substantially occupy the entire inerior volume of the receptacle. Defoamer 30 is a generally porous material which preferably has been treated with a surfactant (a surface-active agent which reduces surface tension). Thus, as blood flows through defoamer 30, the surface tension of any air bubbles suspended within the blood is reduced, thereby causing the bubbles to burst so as to release the suspended air from the blood. Defoamer 30 is preferably formed of either a foam-like substance having a substantially uniform porosity (such as a polyurethane foam) or a fibrous mass composed, for example, of stainless steel or polypropylene filament, although defoamer 30 could also be formed of other materials, such as, for example, small beads of glass or teflon.

The surfactant coating is applied to the defoamer material by soaking the defoamer material in either freon or carbon tetrachloride which is mixed with a chemical surfactant, such as "Antifoam A," which is well known in the industry and commercially available from Dow Chemical. When the defoamer material is removed from this solution, the freon or carbon tetrachloride evaporates, leaving the desired surfactant coating the porous defoamer material. A presently preferred embodiment of defoamer 30 is formed of polyurethane foam which is treated according to the above method.

A presently preferred embodiment of defoamer 30, as illustrated in FIG. 3, includes three layers of defoamer material 30a, 30b and 30c. Each of layers 30a, 30b and 30c have different densities, with layer 30a having the lowest density and layer 30c having the highest density. Accordingly, layers 30a, 30b and 30c will have porous openings of different sizes, with layer 30a having porous openings which are generally the largest and layer 30c having porous openings which are generally the smallest.

Layer 30a may advantageously be formed by cutting out a plurality of plies from a sheet of defoamer material which has the desired density and porosity and which has been coated with a surfactant as described above. Each of the plies are cut out so as to conform to the interior shape of cardiotomy reservoir 10, and the plies are then stacked on top of each other until the desired thickness for layer 30a is achieved. Layers 30b and 30c may be formed in a simliar manner, using sheets of defoamer material having different densities and porosities from the sheet of material which was used to form layer 30a. Thus, defoamer 30 may be easily manufactured and quickly assembled into cardiotomy reservoir 10.

For some applications, it may be desirable to use a gross filter (not shown) in connection with cardiotomy reservoir 10 and adjacent to inlets 20 in order to remove large pieces of foreign matter from the blood, such as tissue, blood clots, and bone wax. In such cases, the gross filter could be attached to inlet ports 20 on the exterior of cardiotomy reservoir 10 or such gross filter could be included within cardiotomy reservoir 10 so as to conform to the interior shape of cardiotomy reservoir 10 and be immediately adjacent to inlet ports 20. A suitable range for the mesh size of such gross filter is from between about 160 microns to about 200 microns. A presently preferred gross filter has a mesh size of about 180 microns.

Figure 4:
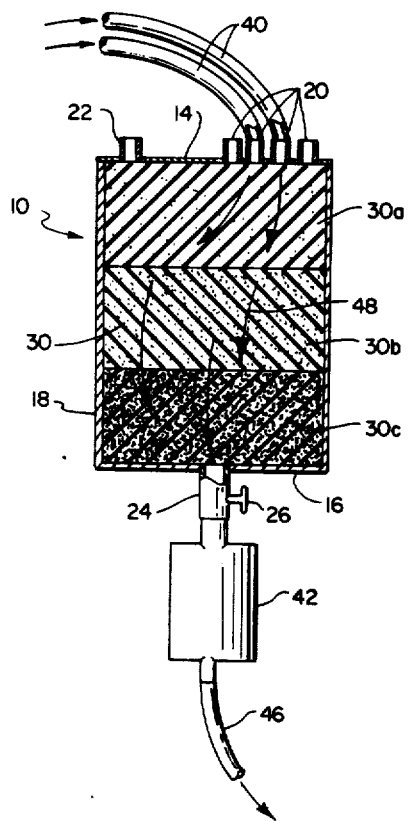
FIG. 4 is a vertical cross-sectional view of a preferred embodiment of the cardiotomy reservoir of the present invention wherein a filter is attached to the outlet, two inlet lines are attached to the inlets, and arrows indicating the direction of flood flow are illustrated.
Figure 5:
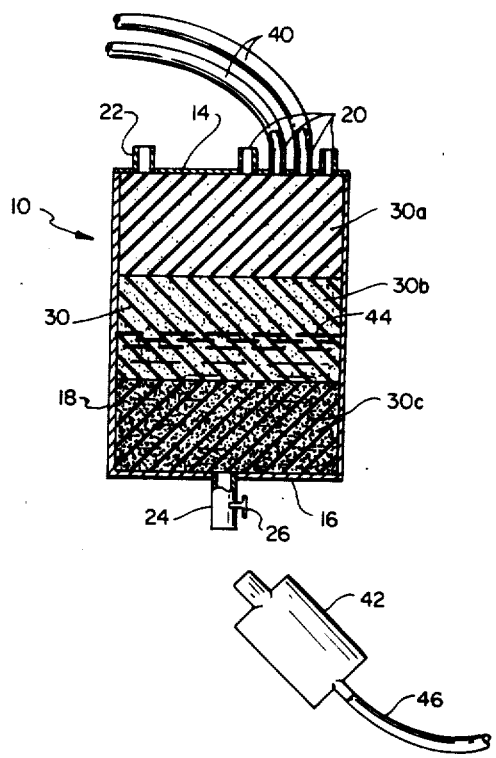
FIG. 5 is a vertical cross-sectional view of a preferred embodiment of the cardiotomy reservoir of the present invention such that outflow of blood from the cardiotomy reservoir is restricted.

The flow of blood through cardiotomy reservoir 10 can best be understood by particular reference to FIG. 4. Intake lines 40 are attached to inlet ports 20 so that as blood is aspirated from the operation site, the blood proceeds through intake lines 40 and into cardiotomy reservoir 10 through inlet ports 20 as indicated by arrows 48 in FIG. 4. Upon entering cardiotomy reservoir 10, the blood passes through layers 30a, 30b and 30c of defoamer 30. As the aspirated blood passes through defoamer 30, the surfactant coating of defoamer 30 reduces the surface tension of the air bubbles suspended within the blood such that the air bubbles burst and the suspended air is liberated and escapes from cardiotomy reservoir 10 through vent port 22. The blood, which has virtually all of the air bubbles removed, exits cardiotomy reservoir 10 through outlet port 24.

An external filter 42 is attached to outlet port 24 so that when valve 26 is in the open position, blood exits the receptacle through outlet port 24 and passes through external filter 42 before entering the main extracorporeal cardiopulmonary by-pass circuit (see FIG. 1). As the blood passes through external filter 42, substantially all of the smaller foreign matter and debris suspended therein (e.g., small pieces of tissue and small blood clots) is removed. A desirable range for the mesh size of external filter 42 is from between about 20 microns to about 40 microns.

If external filter 42 becomes clogged during the course of the operation, external filter 42 may be replaced easily and without significant loss of time or blood. As shown in FIG. 4, valve 26 may be closed to prevent blood from flowing through outlet port 24. External filter 42 may then be removed from outlet port 24 and replaced with a new filter. During the time that fluid flow is occluded through outlet port 24, the blood inside cardiotomy reservoir 10 is continuously in contact with defoamer 30. Thus, defoamer 30 continues to defoam blood 44 during the time that external filter 42 is being changed. Once external filter 42 has been replaced and reattached to outlet port 24, valve 26 may be opened again allow blood 44 to flow through outlet port 24 and external filter 42 to the main extracorporeal circuit.

If, during the course of the operation, it is observed that blood is flowing through cardiotomy reservoir 10 too rapidly to allow adequate defoaming, valve 26 may be intermittently closed to allow blood to pool in cardiotomy reservoir 10. Again, when valve 26 when is closed, all of the blood within cardiotomy reservoir 10 is in contact with defoamer 30. Thus, all of the blood within cardiotomy reservoir 10 continues to be defoamed until valve 26 is turned to the open position, permitting free fluid flow through outlet port 24. This procedure may be repeated as required, in order to insure adequate defoaming of the aspirated blood.

From the above discussion, it will be appreciated that the present invention provides a cardiotomy reservoir which is effective in defoaming blood aspirated from a patient during surgery. By having a defoamer which is graduated in density, the cardiotomy reservoir of the present invention specifically provides for effective defoaming of blood having a wide variety of sizes and quantities of air bubbles suspended therein. Since the defoamer completely fills the interior volume of the cardiotomy reservoir, the blood within the reservoir is constantly in contact with the defoaming element, thereby maximizing the defoaming accomplished within the reservoir. By placing a valve on the outlet of the cardiotomy reservoir and by using an external blood filter between the cardiotomy reservoir and the oxygenator, an occluded filter may be rapidly replaced and the blood loss caused thereby, minimized. The present invention, thus, provides a method for defoaming blood which is effective in removing air bubbles from aspirated blood and which minimizes the danger to the patient incident to the defoaming process.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A cardiotomy reservoir for use in an extracorporeal blood circuit, said cardiotomy reservoir comprising:
    a receptacle for receiving blood from a patient, said receptacle having at least one inlet through which the blood enters the receptacle and an outlet through which the blood exits the receptacle;
    means within said receptacle for defoaming the blood such that a portion of said defoaming means in the proximity of said inlet has a density which is less than a density of a portion of said defoaming means in the proximity of said outlet, thereby resulting in said defoaming means having an increasing density in the direction of blood flow through the receptacle, said defoaming means substantially occupying the entire interior volume of the receptacle such that the blood is in substantial contact with the defoaming means throughout its residence in the receptacle;
    means for filtering foreign matter from the blood, said filtering means being in fluid communication with said outlet of the receptacle; and
    means interposed between the receptacle and the filtering means for selectively interrupting the flow of blood from the outlet of the receptacle into the filtering means, said means furthering allowing for replacement of said filtering means with a minimal loss of time and blood and without significantly disturbing the blood within the receptacle.

2. A cardiotomy reservoir for use in an extracorporeal blood circuit as defined in claim 1 wherein said blood defoaming means has porous openings such that the portion of said blood defoaming means having a greater density has porous openings which are smaller than the portion of said blood defoaming means having a lesser density.

3. A cardiotomy reservoir for use in an extracorporeal blood circuit as defined in claim 1 wherein said filtering means has an effective mesh size within the range of between about 20 microns and about 40 microns.

4. A cardiotomy reservoir for use in an extracorporeal blood circuit as defined in claim 1 wherein said receptable is formed of hard plastic material.

5. A cardiotomy reservoir for use in an extracorporeal blood circuit as defined in claim 4 wherein said hard plastic material is polycarbonate.

6. A cardiotomy reservoir for use in an extracorporeal blood circuit as defined in claim 1 wherein said receptacle is formed of a transparent plastic material.

7. A cardiotomy reservoir for use in an extracorporeal blood circuit as defined in claim 1 wherein said blood defoaming means is formed of a plurality of layers of defoaming material.

8. A cardiotomy reservoir for use in an extracorporeal blood circuit as defined in claim 7 wherein said defoaming material is a foam substance coated with a surfactant.

9. A cardiotomy reservoir for use in an extracorporeal blood circuit as defined in claim 8 wherein said foam substance is polyurethane.

10. A cardiotomy reservoir for use in an extracorporeal blood circuit as defined in claim 7 wherein said defoaming material is a fibrous substance coated with a surfactant.

11. A cardiotomy reservoir for use in an extracorporeal blood circuit as defined in claim 10 wherein said fibrous substance is a mass of polypropylene filament.

12. A cardiotomy reservoir for use in an extracorporeal blood circuit as defined in claim 10 wherein said fibrous substance is a mass of stainless steel filament.

13. A cardiotomy reservoir for use in an extracorporeal blood circuit as defined in claim 7 wherein said plurality of layers comprise at least three layers, each having densities different from each other.

14. A cardiotomy reservoir for use in an extracorporeal blood circuit as defined in claim 13 wherein said layers have porous openings and the porous openings in said layers having a greater density are smaller than the porous opening in said layers having a lesser density.

15. A cardiotomy reservoir for use in an extracorporeal blood circuit as defined in claim 13 wherein each of said layers comprise a plurality of plies of said defoaming material, said plies being stacked on top of each other.

16. A cardiotomy reservoir for use in an extracorporeal blood circuit as defined in claim 13 wherein said layers are arranged within said receptacle such that the density of said layers increases in the direction of blood flow through the receptacle.

17. A cardiotomy reservoir for use in an extracorporeal blood circuit as defined in claim 1 further comprising a vent port which allows the air which has been released from the blood to exit said receptacle.

18. A cardiotomy reservoir as defined in claim 1 further comprising a gross filter which is located in the blood circuit such that blood passes through said gross filter before it comes in contact with said blood defoaming means.

19. A cardiotomy reservoir for use in an extracorporeal blood circuit as defined in claim 18 wherein said gross filter has a mesh size which is within the range of between about 160 microns and about 200 microns.

20. A cardiotomy reservoir for use in an extracorporeal blood circuit as defined in claim 18 wherein said gross filter is located inside said receptacle substantially adjacent to said inlet of the receptacle.

21. A cardiotomy reservoir for use in an extracorporeal blood circuit as defined in claim 18 wherein said gross filter is located outside said receptacles and communicates with said inlet of the receptacle.

22. A cardiotomy reservoir for use in an extracorporeal blood circuit, said cardiotomy reservoir comprising:
a receptacle for receiving blood from a patient, said receptacle having an inlet at one end of said receptacle through which the blood enters the receptacle and an outlet at an opposite end of said receptacle through which the blood exits the receptacle;
means within said receptacle for defoaming the blood, said defoaming means extending from said inlet of the receptacle to said outlet of the receptacle, and a portion of said defoaming means in the proximity of said inlet having a density which is less than a density of a portion of said defoaming means in the proximity of said outlet, thereby resulting in said defoaming means having an increasing density in the direction of blood flow through the receptacle, said blood defoaming means having porous openings such that the portion of said defoaming means having a greater density has porous openings which are smaller than the portion of said blood defoaming means having a lesser density;
means for filtering foreign matter from the blood, said filtering means being in fluid communication with said outlet of the receptacle; and
means interposed between the receptacle and the filtering means for selectively interrupting the flow of blood from the outlet of the receptacle into the filtering means, said means for selectively interrupting the flow of blood serving to allow for replacement of said filtering means with a minimal loss of time and blood and without significantly disturbing the blood within the receptacle.

23. A cardiotomy reservoir for use in an extracorporeal blood circuit as defined in claim 22, wherein said blood defoaming means substantially occupies the entire interior volume of the receptacle such that the blood is in substantial contact with the defoaming means throughout its residence in the receptacle.

24. A cardiotomy reservoir for use in an extracorporeal blood circuit as defined in claim 22 further comprising a vent port which allows the air which has been released from the blood to exit said receptacle.

25. A cardiotomy reservoir as defined in claim 22 further comprising a gross filter which is located in the blood circuit such that blood passes through said gross filter before it comes in contact with said blood defoaming means.

26. An extracorporeal blood circuit for use during surgery on a patient, said extracorporeal blood circuit comprising:
aspirating means for removing blood and foreign matter from the patient at the surgical site;
a receptacle for receiving blood from the patient, said receptacle having an inlet through which the blood enters the receptacle and an outlet rhrough which the blood exits the receptacle;

first blood conveying means connected to said blood aspirating means and to the inlet of said receptacle for conveying the blood from the blood aspirating means to the receptacle;

means for pumping blood through said first blood conveying means and into said receptacle;

means within said receptacle for defoaming the blood such that a portion of said defoaming means in the proximity of said inlet has a density which is less than a denstiy of a portion of said defoaming means in the proximity of said outlet, thereby resulting in said defoaming means having an increasing density in the direction of blood flow through the receptacle;

an oxygenator for oxygenating the blood before it is returned to the patient;

second blood conveying means connected to the outlet of said receptacle and to said oxygenator for conveying blood from the receptacle to the oxygenator;

means positioned along said second blood conveying means for filtering foreign matter from the blood, said filtering means being in fluid communication with said outlet of the receptacle;

valve means interposed along said second blood conveying means between the receptacle and the filtering means for selectively interrupting the flow of blood from the outlet of the receptacle into the filtering means, said means for selectively interrupting the flow of blood serving to allow for replacement of said filtering means with a minimal loss of time and blood and without significantly disturbing the blood within the receptacle; and third blood conveying means connected to said oxygenator for conveying blood from the oxygenator to the patient.

27. An extracorporeal blood circuit for use during surgery on a patient as defined in claim 26 wherein said blood defoaming means has porous openings such that the portion of said blood defoaming means having a greater density has porous openings which are smaller than the portion of said blood defoaming means having a lesser density.

28. An extracorporeal blood circuit for use during surgery on a patient as defined in claim 26 wherein said blood defoaming means extends from one end of the receptacle to an opposite end of the receptacle.

29. An extracorporeal blood circuit for use during surgery on a patient as defined in claim 28 wherein said blood defoaming means substantially occupies the entire interior volume of the receptacle such that the blood is in substantial contact with the defoaming means throughout its residence in the receptacle.

30. A cardiotomy reservoir for use in an extracorporeal blood circuit, said cardiotomy reservoir comprising:

a generally cylindrical vessel for receiving blood from a patient, said vessel being formed of a hard, transparent plastic material and having a plurality of inlets at one end of said vessel through which the blood enters the vessel and an outlet at an opposite end of said vessel through which the blood exits the vessel and a vent port through which air that is released from the blood exits the vessel;

means within said vessel for defoaming the blood, said defoaming means extending from said one end of the vessel to said opposite end of the vessel and substantially occupying the entire interior volume of the vessel, said defoaming means further being such that a portion of said defoaming means in the proximity of said inlet has a density which is less than a density of a portion of said defoaming means in the proximity of said outlet, thereby resulting in said defoaming means having an increasing density in the direction of blood flow through the vessel, said defoaming means also having porous openings such that the portion of said defoaming means having a greater density has porous openings which are smaller than the portion of said defoaming means having a lesser density;

means for filtering foreign matter from the blood, said filtering means being in fluid communication with said outlet of the receptacle; and means interposed between the receptacle and the filtering means for selectively interrupting the flow of blood from the outlet of the receptacle into the filtering means, said means for selectively interrupting the flow of blood serving to allow for replacement of said filtering means with a minimal loss of time and blood and without significantly disturbing the blood within the receptacle.

31. A cardiotomy reservoir for use in an extracorporeal blood circuit as defined in claim 30 wherein said hard, transparent plastic material is polycarbonate.

32. A cardiotomy reservoir for use in an extracorporeal blood circuit as defined in claim 30 wherein said blood defoaming means is formed of a plurality of layers of polyurethane foam which is coated with a surfactant.

33. A method for defoaming blood in an extracorporeal blood circuit, said method comprising the steps of:

obtaining blood having air bubbles suspended therein;

collecting the blood in a receptace having an inlet and an outlet;

defoaming the blood by passing the blood through a blood defoaming means within the receptacle, a portion of said defoaming means in the proximity of said inlet having a density which is less than a density of a portion of said defoaming means in the proximity of said outlet, thereby resulting in said defoaming means having an increasing density in the direction of blood flow, said defoaming means reducing the surface tension of the air bubbles thereby causing said air bubbles to break so as to separate substantially all of the air from the blood;

removing the air which has been separated from the blood through a vent means formed in said receptacle;

removing the blood from the receptacle, said blood having substantially all of the air bubbles removed from it;

passing the blood removed from the receptacle into a filtering means so as to filter out foreign matter from the blood; and interposing valve means between said outlet of the receptacle and said filtering means, said valve means serving to selectively interrupt the flow of blood from said outlet of the receptacle into said filtering means, said valve means further serving to allow for replacement of said filtering means with a minimal loss of time and blood and without significantly disturbing the blood within the receptacle.

* * * * *

UNITED STATES PATENT AND TRADEMARK OFFICE
CERTIFICATE OF CORRECTION

PATENT NO. : 4,704,203

DATED : November 3, 1987

INVENTOR(S) : Charles C. Reed

It is certified that error appears in the above-identified patent and that said Letters Patent is hereby corrected as shown below:

Column 1, line 15, "are" should be --is--
Column 1, line 30, "heat" should be --heart--
Column 2, line 26, "are" should be --is--
Column 2, line 46, "filtr" should be --filter--
Column 2, line 65, "surgery, Additionally," should be --surgery. Additionally,--
Column 3, line 39, "dnager" should be --danger--
Column 4, line 17, "flood" should be --blood--
Column 5, line 65, "rollers" should be --roller--
Column 7, line 14, "between" should be deleted
Column 7, line 42, "between" should be deleted
Column 7, line 64, "when valve 26 when is" should be --when valve 26 is--
Column 8, line 61, "furthering allowing" should be --further allowing--
Column 9, lines 40-41, "said plurality of layers comprise" should be --said plurality of layers comprises--
Column 9, line 47, "opening" should be --openings--
Column 9, lines 49-50, "each of said layers comprise" should be --each of said layers comprises--
Column 10, line 9, "receptacles" should be --receptacle--
Column 10, line 67, "rhrough" should be --through--
Column 11, line 10, "denstiy" should be --density--

Signed and Sealed this

Fifth Day of July, 1988

Attest:

DONALD J. QUIGG

Attesting Officer

Commissioner of Patents and Trademarks